(12) United States Patent
Reyes

(10) Patent No.: US 10,136,975 B2
(45) Date of Patent: Nov. 27, 2018

(54) ORAL CAVITY SUCTION SYSTEM

(71) Applicant: Hari Mark Reyes, Portland, OR (US)

(72) Inventor: Hari Mark Reyes, Portland, OR (US)

( * ) Notice: Subject to any disclaimer, the term of this patent is extended or adjusted under 35 U.S.C. 154(b) by 258 days.

(21) Appl. No.: 15/265,762

(22) Filed: Sep. 14, 2016

(65) Prior Publication Data

US 2017/0156833 A1 Jun. 8, 2017

Related U.S. Application Data

(63) Continuation-in-part of application No. 15/146,567, filed on May 4, 2016, now Pat. No. 9,956,062.

(60) Provisional application No. 62/263,867, filed on Dec. 7, 2015.

(51) Int. Cl.
*A61C 17/06* (2006.01)
*A61C 5/14* (2006.01)

(52) U.S. Cl.
CPC .............. *A61C 17/043* (2013.01); *A61C 5/14* (2013.01)

(58) Field of Classification Search
CPC ..................... A61C 17/00–17/043; A61C 5/14
USPC ...................... 433/91–96; 604/19; 285/134.1, 285/135.1–135.4, 136.1, 137.11
See application file for complete search history.

(56) References Cited

U.S. PATENT DOCUMENTS

| | | | | |
|---|---|---|---|---|
| 1,417,395 A | * | 5/1922 | Lassiter | B21C 37/283 16/212 |
| 2,409,023 A | * | 10/1946 | Dies | B21C 37/283 285/134.1 |
| 4,017,975 A | * | 4/1977 | Johnson | A61C 17/043 433/91 |
| 9,283,308 B2 | * | 3/2016 | Hajarian | A61M 1/008 |
| 2014/0349249 A1 | * | 11/2014 | Reyes | A61C 17/043 433/96 |

\* cited by examiner

*Primary Examiner* — Yogesh Patel
(74) *Attorney, Agent, or Firm* — Mark S Hubert

(57) ABSTRACT

An oral cavity suction system that incorporates a disposable saliva ejector residing along the interior of the patient's cheek that utilizes a single planar, double leaf shaped plate design that is embossed on their inner faces with a series of arced ribs and folded about its midpoint. The arced ribs form a series of channels about perimeter of the device that directs saliva into a trough running along the linear axis of both of the plates to direct this saliva into a connected "U" connector that hooks around the patient's cheek. A sterile suction tube is also connected on one end to the "U" connector suction tube and on its other end to a quick connect fitting that mates to a tube adapted with a fitting for connection to a high volume suction pump.

16 Claims, 7 Drawing Sheets

FIG. 4
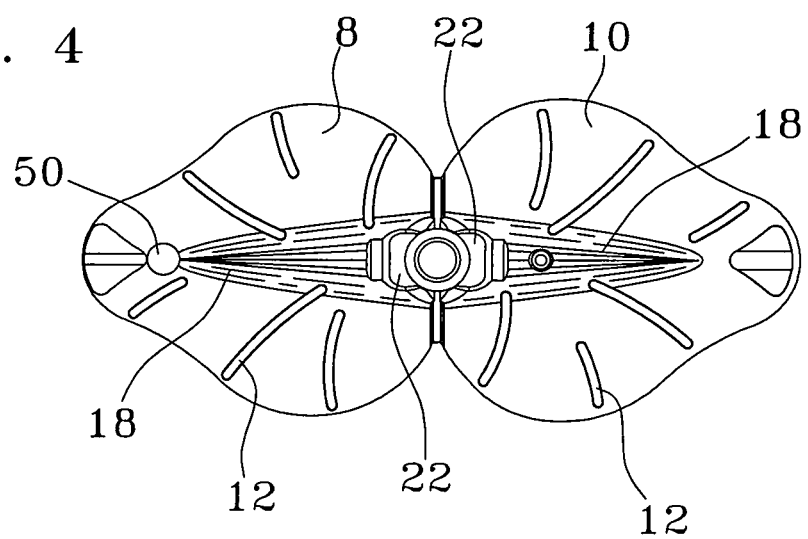
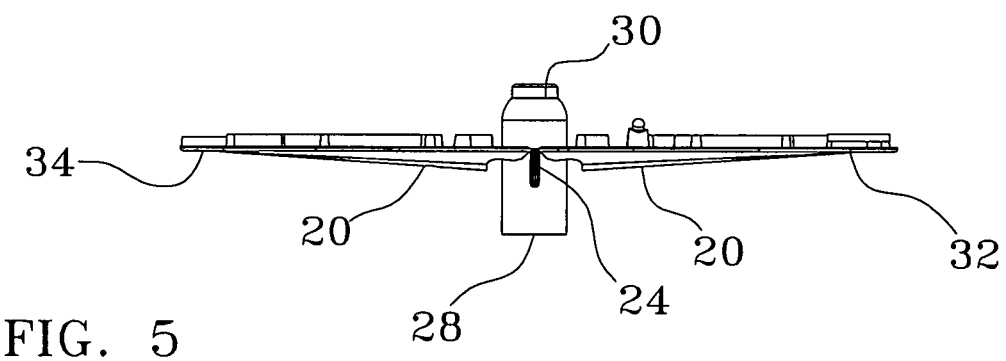
FIG. 5
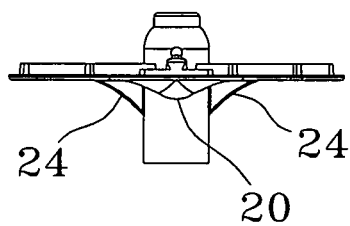
FIG. 6

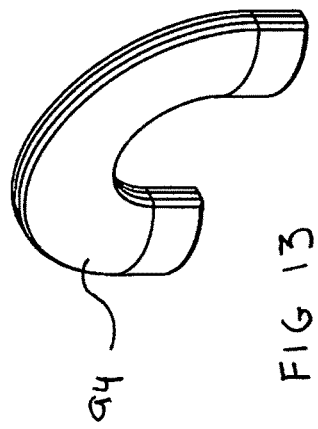
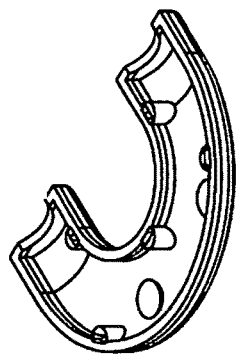
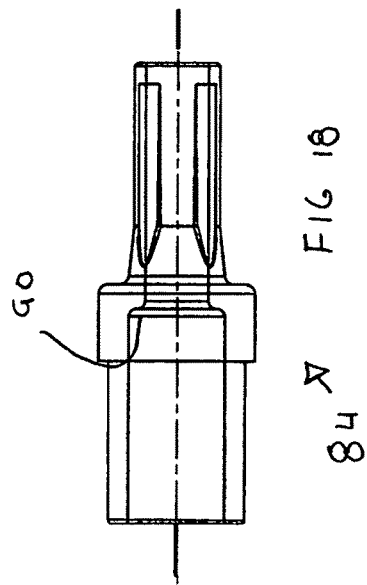
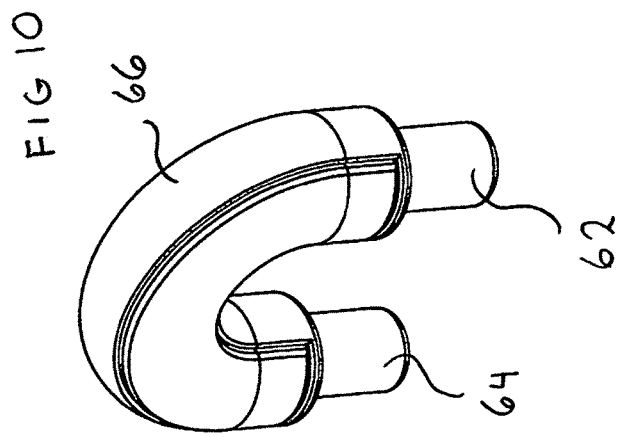

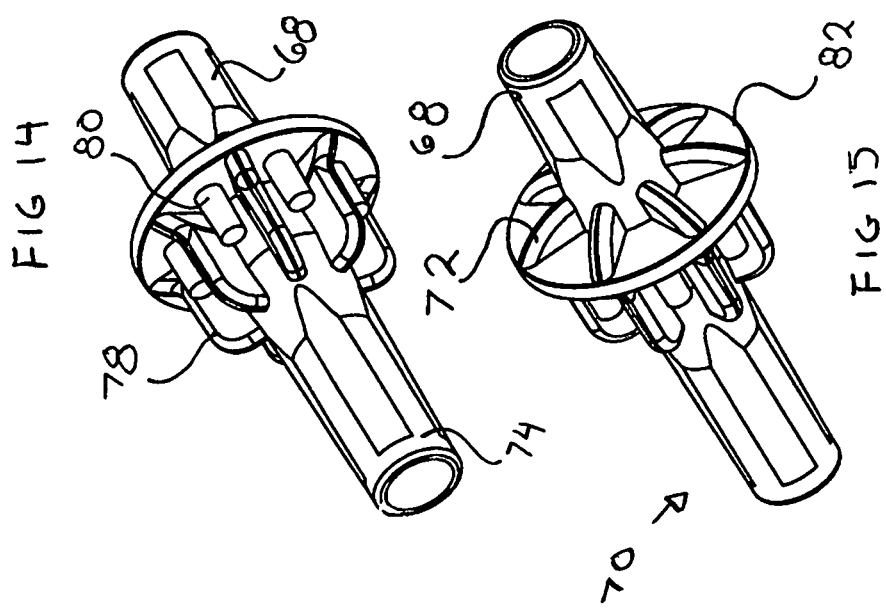

ORAL CAVITY SUCTION SYSTEM

PREVIOUS APPLICATIONS

This patent is a Continuation in Part of pending U.S. Utility application Ser. No. 15/146,567 filed May 4, 2016 Entitled "IMPROVED ORAL CAVITY SUCTION DEVICE" and incorporates it in its entirety herein by reference. This also claims priority from provisional patent 62/263,867 titled the same and filed Dec. 7, 2015.

COPYRIGHT STATEMENT

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

FIELD

The present disclosure relates, in general, to an oral cavity suction system, and more particularly to a set of hoses, and three different quick connect couplings connectable to a dental saliva ejection device for a sanitary saliva ejection system.

BACKGROUND

Oral cavity suction devices, also known as saliva ejectors are narrow vacuum tubes that dental health professionals employ for removing saliva, water, and debris during a dental procedure. Often saliva ejectors will "sit" in a patient's mouth during a dental procedure in order to continuously rid the mouth of excess saliva, water, and debris to facilitate uninterrupted work by the dental health professional. The ejector tubes are typically made of a pliable plastic with a metal wire embedded within its wall to allow the tube to be bent to a desired angle and maintain that angle. If the tip of the suction tube contacts the patient's mouth tissue, it can suck the tissue into contact with the tip of the ejector, thereby rendering the ejector useless, since it is no longer removing excess saliva, water, and debris, not to mention causing a very uncomfortable sensation for the patient. Due to this fact the dentist preforming the work on the patient must be assisted at all times.

Further, most dental saliva ejection devices are replaceable, disposable polymer straws with an angled distal end that has its proximal end connectable to a 5/32" internal diameter tube suction tube, which is coupled to a vacuum pump. These devices must be manually entered into the patient's mouth periodically. Cross contamination is possible, separated only by the length of straw used. Additionally, the tubing must run inconveniently, between the patient and the dentist/dental assistant.

A disposable, cost effective, comfortable, and efficient saliva ejector system, reusable parts of which can be sanitized between patients for reuse and that that can be managed in a patient's mouth without the need for a dental assistant, with a vacuum tubing routing that is out of the way of the dentist's/dental assistant's work space, would be a welcome addition to the dental industry. Such a system is provided by the embodiments set forth below.

BRIEF SUMMARY

In accordance with various embodiments, an improved saliva ejection system, with increased suction potential, is provided.

The saliva ejector system of the saliva ejection system solves the aforementioned problems by employing a tapered, ovate shape foldable saliva ejector that is connectable to a quick connect U shaped cheek coupling so as to allow the associated vacuum tubing to run back along the outside of the patient's cheek and out of the way of the patient and the dentist. The saliva ejector of the present invention resides along the left or right-side buccal mucosa allowing for full view of the oral cavity. When the saliva ejector is positioned along the buccal mucosa, it alleviates the patient's natural gag reflex, and is out of the way of most dental procedures. Since the system utilizes a larger diameter tubing, a high volume suction pump, and the saliva ejector has a plethora of arced passages formed about its perimeter (when assembled), and is non collapsible, it can accommodate a larger than conventional suction field where it is needed, yet does not tug on the patient's buccal mucosa and inner cheek. The ejector's slender profile aids in positioning the saliva ejector within the patient's mouth, resulting in a more effective, gentler and comfortable saliva ejector. When coupled to a suction tube with a "U" bend quick connector coupling, a sort section of surgical suction tubing, a straight quick connect coupling and another, longer section of tubing connected to the suction pump, the system may be disconnected at the straight quick connect coupling and the removed components, autoclaved until sterile for reuse. This entire combination may be placed adjacent the outside of the patient's cheek with the remaining tubing running back below the patient's ear such that the entire oral cavity suction system (the saliva ejector, the quick connects and the suction tubing) is out of the dentist's way and requires little if any attention. Since the tubing back to the straight quick connect coupling can quickly be removed and replaced, it and the U shaped cheek coupling may be removed, replaced and put into an autoclave for sterilization.

The patient can easily adjust his bite without the removal of the suction system, as well as relieve the water/saliva from his mouth by simply closing his mouth, thereby allowing the dentist or hygienist to work without an assistant constantly providing suction.

The saliva ejector of the saliva ejection system also maximizes the patient's comfort if he has lingual gum sensitivity, temporomandibular joint (TMJ) issues, or mandibular or maxillary tori; these regions are simply not contacted due to the device's unique geometry, and its placement within the mouth.

The saliva ejector of the saliva ejection system allows simplified fabrication and assembly of the device. It allows a planar fabrication and assembly about the axial centerline of the device. The processes utilized in fabrication are simplified and the number of fabrication steps are reduced.

The saliva ejection system of the present invention allows for larger diameter suction tubing (with thicker, non-collapsable walls) to accommodate higher suction draw and capacity.

Various modifications and additions can be made to the embodiments discussed without departing from the scope of the invention. For example, while the embodiments described above refer to particular features, the scope of this invention also includes embodiments having different combination of features and embodiments that do not include all of the above described features.

BRIEF DESCRIPTION OF THE DRAWINGS

A further understanding of the nature and advantages of particular embodiments may be realized by reference to the remaining portions of the specification and the drawings, in which like reference numerals are used to refer to similar components.

FIG. 4 is a top view of the unassembled saliva ejector;

FIG. 5 is a right side view of the unassembled saliva ejector;

FIG. 6 a first end view of the unassembled saliva ejector;

FIG. 10 is a perspective side view of the assembled "U" connector;

FIG. 12 is an inside perspective view of a "U" connector side plate;

FIG. 13 is a front perspective view for a "U" connector side plate;

FIG. 14 is a rear perspective view of the quick connect straight coupling;

FIG. 15 is a front perspective view of the quick connect straight coupling;

FIG. 18 is a side cross sectional view of a vacuum machine coupling; and

DETAILED DESCRIPTION OF CERTAIN EMBODIMENTS

Figure 1:
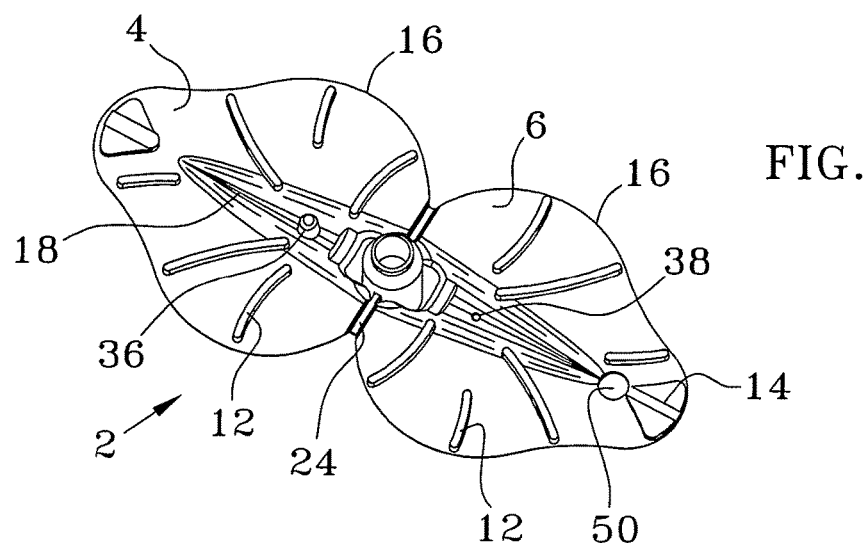
FIG. 1 is a top perspective view of the unassembled saliva ejector.

Looking at FIG. 1 it can be seen that the saliva ejector 2 is a pair of substantially planar, similar leaf shaped (ovate) plates with their proximal ends hingedly connected together into a mirror image configuration with a short tube extending normally above and below the plates from a cutout region at the center of the ejector's axial centerline, where the two plates are conjoined. When assembled, by virtue of interlocking dovetailed raised pads at the tip of each ovate plate and a central circular tab and slot, the conjoined ovate plates define a salvia flow system that allows the evacuation of the salvia from the device via a suction/vacuum system. (The saliva flow system is made of a series of flow channels and a central trough.) However, upon closer examination it can be seen that this device is much more structurally complex as will be discussed herein. (It is to be noted that vacuum and suction are used interchangeably herein.)

Figure 17:
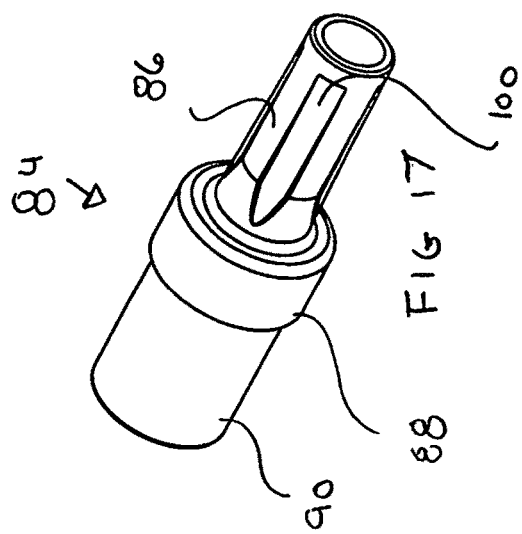
FIG. 17 is a side perspective of a vacuum machine coupling.
Figure 19:
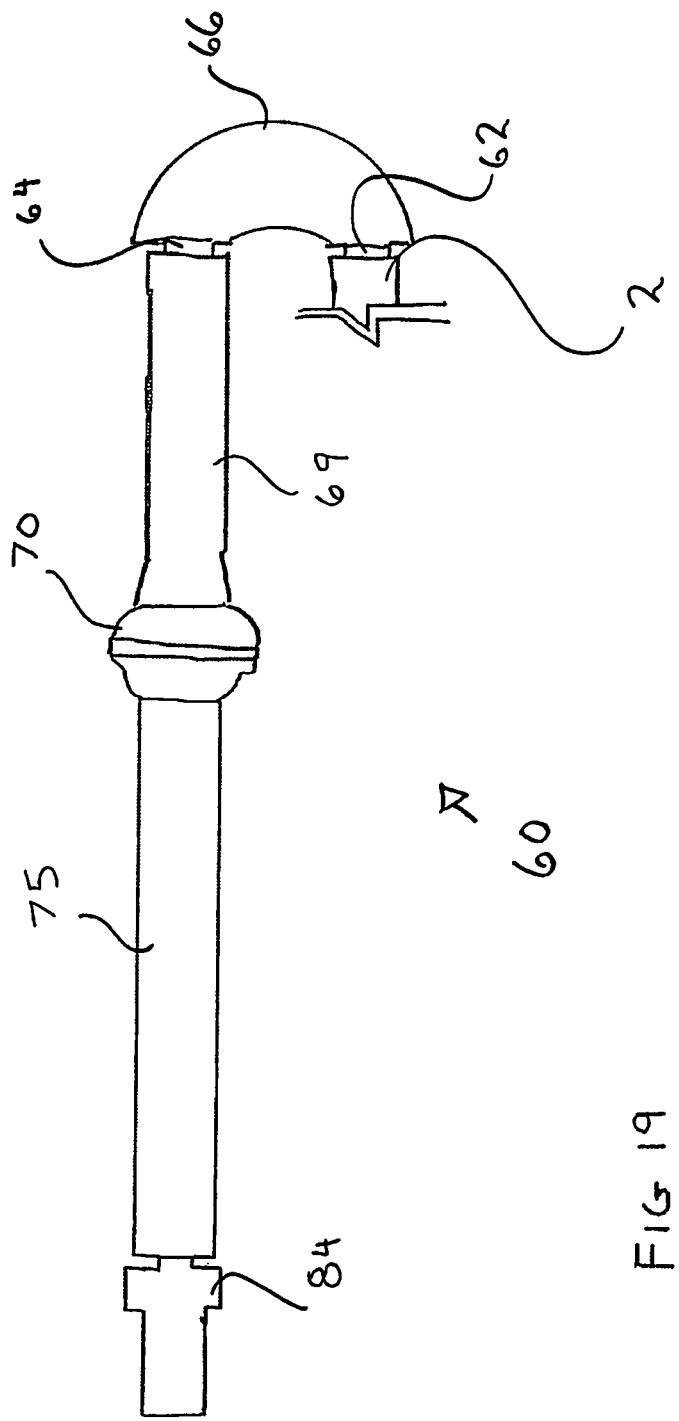
FIG. 19 is a side view of the assembled saliva ejection system with the saliva ejector only partially shown for visual clarity.

The saliva ejection system 60 (FIG. 19) is made of a saliva ejector 2 (only partially illustrated for visual clarity) that has its vacuum connection end 28 at the exterior of the circular connection tube 26 frictionally stretched (elastically deformed) over the interior cheek nipple 62 of the "U" connector 66. (FIG. 10) Frictionally stretched over the exterior cheek nipple 64 of the "U" connector 66 is the distal end of medical grade, sterile suction tube 68. This section of tubing is approximately 6-12 inches in length and is frangible such that it can be sized to fit into the specific size of autoclave that dentist uses. The proximal end of the sterile tube 69 is frictionally stretched over the short entrance nipple 68 of the straight quick connect coupling 70 (FIGS. 14-16) and abutted to the front stop ribs 72. The distal end of the non-sterile vacuum tube 75 is frictionally stretched over the long, exit nipple 74 of the straight quick connect coupling 70, over the stretcher ribs 78 and stretcher pegs 80, and abutted to the rear face of the central flange 82. The proximal end of the non-sterile vacuum tube 75 has the minor nipple 86 of a vacuum fitting 84 (FIGS. 17 and 18) inserted into its interior diameter until the non-sterile tube abuts the flange ring 88. The major nipple 90 of the vacuum fitting 84 is sized to internally accept a standard inlet nipple of a high volume vacuum pump (generally 0.305 inches) which is inserted until the inlet nipple abuts the interior shoulder 90.

Looking at FIGS. 10-13 it can be seen that the "U" connector 66 that the vacuum connection end of the of the connection tube 26 connects to is a hollow shell fitting 92 that is semi circular about its center (with a 0.218 inch inner radius), and with a preferred outer diameter of 1.250 inches and a length of 0.771 inches. From either end of the shell fitting 92 extends a straight cheek nipple 62 and 64 preferably with an interior diameter of 0.205 inches and and outer diameter of 0.275 inches. (Hence the elastic deformation over the 0.250 inch interior diameter sterile suction tube 69.)

The shell fitting 92 of the "U" connector 66 is sonically welded to a cover plate 94 (FIGS. 12 and 13) to form the "U" connector 66. This design is for fabrication purposes such that there are no seams between the cheek nipples 62 and 64 and the shell fitting 92. It is to be noted that to accomplish this the shell cover plate 94 is not as deep as the centerline and does not extent to the linear axis of the shell fitting 92. The "U" connector 66, like all of the connectors used in the saliva ejection system 60 are made from polycarbonate. This material sterilizes nicely and may be subject to numerous autoclave cycles without failure. The "U" connector and sterile suction tube can be reusable or disposable, although autoclave sterilization is recommended. The saliva ejector 2 however, is intended for single use only.

The sterile suction tube 69 and the non-sterile suction tube 75 preferably are each made of medical grade surgical suction tubing. They differ only in their length and the fact that the sterile suction tube 69 is sterilized between uses. The sterile suction tube 69 resides between the "U" connector 66 and the straight quick connect fitting 70 whereas the non-sterile suction tube 75 resides between the Straight quick connect fitting 70 and the standard inlet nipple of a high volume vacuum pump. Preferably the tubing has an 0.250 inch inner diameter and is of a thick wall elastically deformable surgical grade polymer.

Figure 16:
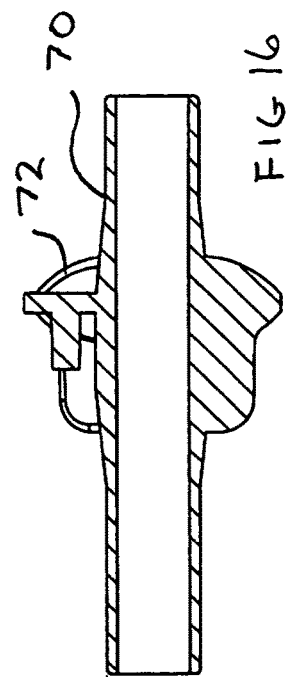
FIG. 16 is a side cross sectional view of the quick connect straight coupling.
Figure 11:
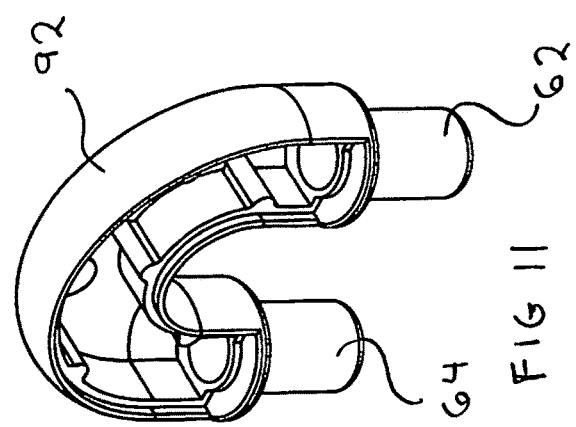
FIG. 11 is a side perspective view of the "U" connector shell.

The straight quick connect coupling 70 FIGS. 14-16 is a linear fitting that has a short entrance nipple 68 on its distal end separated from a long exit nipple 74 on its proximal end by a central flange 82. On the short entrance nipple side of the central flange, extending normally is a set of front radially spaced stop ribs 72. These are approximately quarter circular extensions that stop the proximal end of the sterile suction tube 69 from completely abutting the front face of the central flange. In this way, for removal, the user can get his fingertips or finger nails between the front face of the central flange 82 and the back edge of the sterile suction tube 69 so as to apply force for the removal of the two pieces. In the preferred embodiment the quick connect coupling 70 is 1.750 inches long with an internal diameter of 0.210 inches and the outer diameter of the short and long nipples (without the stop ribs ofor the stretcher ribs is 0.270 inches.

The rear face of the central flange of the straight quick connect coupling 70 has a series of stretcher ribs 78 and stretcher pegs 80 radially spaced about and extending normally therefrom. These stretcher ribs 78 serve to stabilize the device (especially when the sterile suction tube 69 has been removed and is being sterilized) as it hangs from the quick connect fitting in a dental chair carriage (not illustrated). This dental chair carriage is a "C" shaped, (open) funnel rack from which dental instruments can hang. These stretcher ribs 78 rest on the tapered wall of the carriage so as to align the device completely vertical and centered within the "C" configuration of the funnel. The stretcher pegs 80 continue to deepen the circumference of the central flange in the voids between adjacent stretcher ribs 78. The longer stretcher ribs 78 and stretcher pegs 80 allow the central flange to remain thinner while still allowing the device to hang unobtrusively in a vertical position in the carriage.

The vacuum fitting 84 (FIGS. 17 and 18) is a linear coupling also but has a flange ring 88 about its center. On one side of the flange ring 88 is a minor nipple 86 again with a preferred exterior diameter of 0.270 inches for sound frictional engagement with the ¼ inch inside diameter surgical tubing. Also on the exterior surface of the minor nipple 86 is a series of stretcher bars that extent partway from the circular flange 88 toward the end of the minor nipple 86. These serve to increase the compression forces of the stretched non-sterile tube 75, for better retention. On the other side of the flange ring 88 is a major nipple 90. This nipple has an inside diameter of 0.305 inches which is the standardized exterior diameter of many vacuum pumps. Since the interior diameter of the minor nipple is preferably 0.200 inches, there is a reduction in the diameter of major nipple where it meets the minor nipple, approximately in the center of the flange ring 88. The overall length of the vacuum fitting 84 in the preferred embodiment is 1.500 inches.

Figure 8:
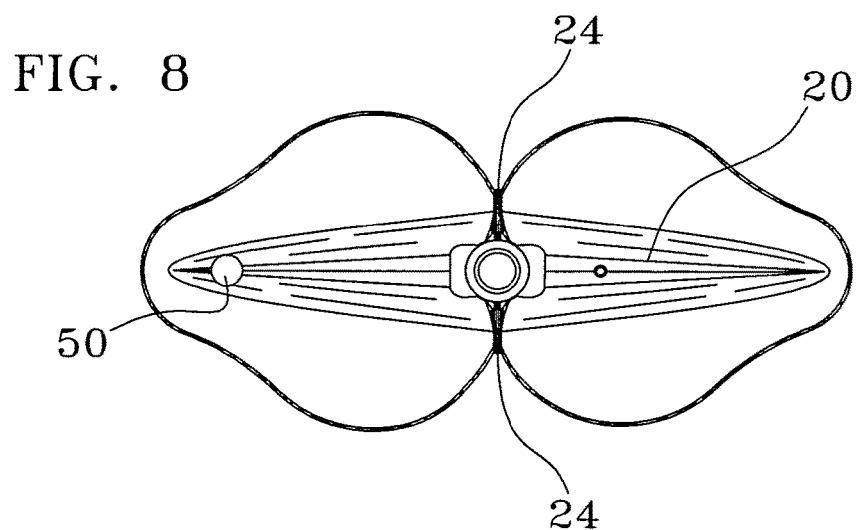
FIG. 8 is a bottom view of the unassembled saliva ejector.
Figure 9:
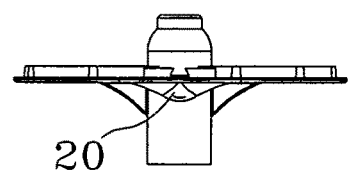
FIG. 9 is a second end view of the unassembled saliva ejector.

There is a unique geometry to the saliva ejector 2, which can generally be described as ovate (i.e., having a wider base than apex and referred to herein also as a leaf shape), such that each plate has two distinct regions, its body 1, and its front lobe 3 (FIG. 8). Combined, these regions are referred to as leaf shaped plates. Each plate is a flexible, generally planar member that is constructed from a medical grade polymer of uniform thickness.

The saliva ejector 2 is made of a first leaf shaped inner plate 4 and a slightly larger, second leaf shaped cheek plate 6. (As denoted, in use, the inner plate 4 faces the patient's mouth's midline and the cheek plate 6 faces the patient's cheek.) The peripheral edges 16 of these two plates trace an identical outline however, these two plates are not identically dimensioned. (In the alternate embodiment, the two plates are identically dimensioned.) In the preferred embodiment, the second, cheek plate 6 is dimensioned so as to be approximately 2 mm larger measured along any line drawn across the device 2. Simply stated, the perimeter edge of the second cheek plate 6 extends approximately 1 mm beyond the perimeter edge of the first inner plate 4.

The plates each are adorned on their interior faces 8 and 10 (FIG. 4) with a series of raised, arced ribs 12 that extend normally therefrom. (As used herein, the term rib refers to any raised projection or embossing extending from the inner faces of the plates.) At the distal ends of each plate there is a raised pad first raised pad 11 on the first plate 4 has a raised dovetail tab 15 formed thereon that matingly conforms to the dovetail slot 14 formed in the second raised pad 13 on the second plate 6. The alignment and mating of these dovetail elements helps keep the two plates 4 and 6 connected at their tip when folded and assembled. In alternate embodiments there may be at least one further slot cut along the second raised pad 13 on the second plate 6 so as to allow for pooled saliva to be drawn from the foremost tip of the device 2 when inserted into a patient's mouth.

It is known that in alternate embodiments other mechanical or chemical means for connecting the tabs may be employed such as gluing, welding, pinning, crimping, slot and tab configurations and the like, which are well known in the field.

Each of the ribs 12 are the same height and width. The top face of the raised pads (excluding the dovetail tab 15) extend approximately only one half of the height from the interior face of the plates that the ribs 12 do. The raised pads serve to define the depth and width of the first channel and keep the tip from collapsing upon itself when suction is applied to the device.

Figure 2:
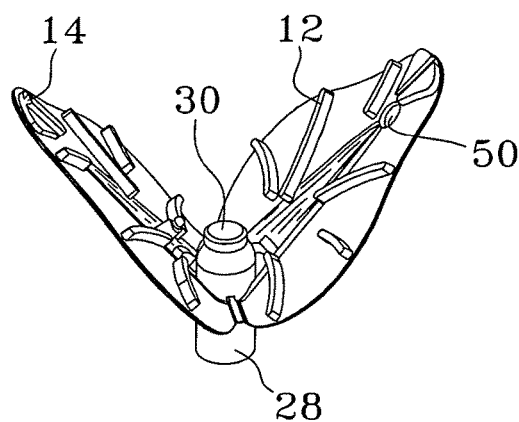
FIG. 2 is a front perspective view of the saliva ejector being assembled.
Figure 3:
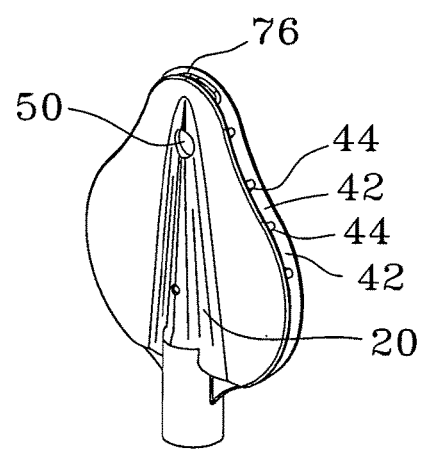
FIG. 3 is a front perspective view of the assembled saliva ejector.
Figure 7:
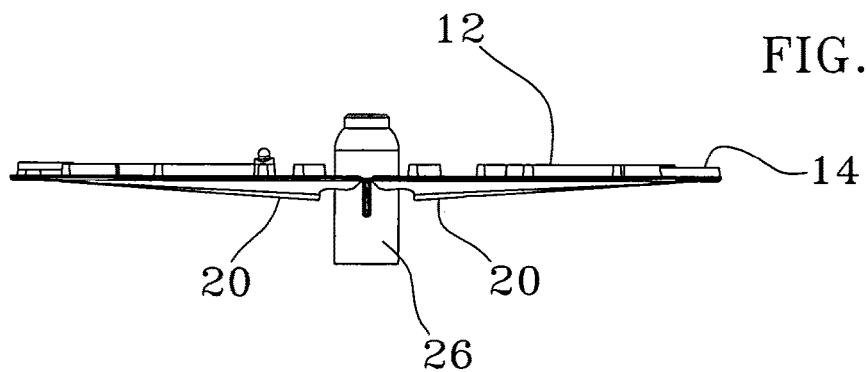
FIG. 7 is a left side view of the unassembled saliva ejector.

Along the linear centerline of each plate is formed an identical trough 18. The troughs 18 are open tapered grooves on the interior faces (FIGS. 1, 2 and 4) that have a raised ridge 20 on the exterior faces 32 and 34 (FIGS. 3, 5, 6, 7, 8 and 9). The taper in the grooves begin at the proximal ends of the plates and extend along the linear centerline but terminate before the raised pads at the distal ends of each plate. The troughs taper in both width and depth, diminishing in these dimensions from the proximal end toward the distal ends. The proximal ends of each plate have a cutout 22 centered about the linear centerline of the plate.

The proximal ends of the two leaf shaped plates are hingedly conjoined together on a pair of triangular gusset supports 24 (FIGS. 5, 6, 7, 8 and 9) that extend from opposite sides of the circular connection tube 26, 180 degrees apart. The gusset supports 24 extend perpendicularly from the axial centerline of the void formed by the joined cutouts 22. Stated otherwise, the gusset supports 24 are formed along the distal end of each of the plates. This is also the axial centerline of the unassembled device. The plane of each of the gusset supports 24 resides perpendicular to the plane of the plates when in the unassembled saliva ejector 2. When the device is assembled, their planes lie parallel but not collinear with each other and the linear axes of the two plates lie parallel in all three planes. The thickness of the gusset supports 24 approximates the height of the ribs. The plates are attached to opposite sides of the gusset supports 24.

There is a suction orifice 50 formed through the first cheek plate 4 (adjacent to the raised pad 14 at the distal end of the plate as is illustrated in FIGS. 1, 2, 3, 4 and 8. This suction orifice 50 coincides with the end of the trough 18 formed on that plate. When the saliva ejector 2 is connected to a suction device and placed properly along the buccal mucosa within the patient's mouth, the inner face of the first cheek plate 4 of the saliva ejector 2 will face toward the midline of the patient's mouth. In this way there will always be suction at the proximal end of the device, either through the suction orifice 50 or the slot 52 in the pad 14 on the second cheek plate 6. This is important, as the tip of the distal end of the device is the point where saliva pools in the patient's mouth.

A vacuum connection end 28 extends from the exterior end of the circular connection tube 26 and a tapered saliva inlet end 30 extends from its interior end when the device 2 is assembled. The vacuum connection end 28 is dimensioned for frictional connection to a suction tube which is operationally connected to a vacuum system. In combination with the saliva ejector 2, these elements form a saliva ejection system.

Centered in the open tapered groove of the trough 18 on the first plate 4 is a circular tab 36 that is matingly conformed for frictional retention in a circular slot 38 that is formed in the open tapered groove 18 on the second plate 6. These along with the dovetail elements on the first and second tabs 11 and 13, are engaged for assembly of the device 2.

When the saliva ejector 2 is assembled (FIG. 2) the cheek plate 6 overlaps the inner plate 4 about its peripheral edges. The saliva inlet end 30 of the connection tube 26 lies inside partially within the cutouts 22 and partially within the tapered groove between the inner faces of the first and second plates. The vacuum connection end 28 extends from the linear centerline of the proximal end of the device. The saliva end matingly conforms for a frictional fit within the open tapered groove. Since the connection tube and the two plates are all made of a flexible polymer, when a suction is applied to the device, these components are drawn together within closer tolerances.

The ribs 12 are arced from the peripheral edge of their respective plates toward the open tapered trough 18 on the interior faces of the plates. The arced ribs 12 do not lie in the same pattern on the two different plates. Rather, the ribs of the two plates lie in symbiotic patterns such that, when the device is assembled and the two plates are folded inward, about the gusset supports 24 (with their inner faces toward each other) so as to reside in a spaced parallel orientation (FIG. 3), a series of adjacent, arced flow channels 42 are formed leading from the peripheral edge 16 of the device to the trough 18. These arced channels 42 are approximately equally spaced about the peripheral edge 40 of the assembled saliva ejector 2, (as are the rib ends 44). Thus, the two plates 4 and 6 in the body of the saliva ejector 2 are supported from collapse (their interior faces being drawn into contact with each other by the vacuum) by the height of the ribs. The distil ends of the saliva ejector 2 are prevented from collapse by the raised pads 14. This ensures that the device will always be able to draw saliva and debris from the channels into the trough 18 and out the connection tube 26.

One of the remarkable features of the physical structure of the saliva ejector 2 is that lends itself to simple, economical production. The entire device is made by injection molding of a flexible dental grade polymer. Since it lays flat prior to assembly the saliva ejector 2 can be stacked for mass shipping.

The device 2 is designed to lie between the buccal regions of the oral cavity and the inner cheek, so as to not rely on teeth for support. The U shaped discharge section of the suction tube curves around the oral commissure and then along the outside of the cheek. The placement of the saliva ejector 2 is key to its function, since saliva pools in the lower regions of the oral cavity toward the throat. When properly placed within a patient's mount, saliva ejector effectively removes the pooled saliva while not impeding the dentist's work. Once placed, saliva ejector is comfortable for the patient and does not need constant monitoring from a dental assistant. The different outer dimensions of the two plates prevent the patient's cheek from being suctioning into contact with the channels. The suction tube is connected to a suction device and once the suction device is turned on a diffuse yet effective suction field is created.

No matter how the teeth are aligned or shaped, or even if the patient has missing teeth, the saliva ejector 2 will be fully supported and still function properly.

In operation, the saliva ejection device 60 is connected to a vacuum pump (preferably a high volume vacuum pump) at the major nipple 88 of the vacuum fitting 84. When the disposable saliva ejector 2 is connected to the straight cheek nipple 92 of the "U" connector 66, and is inserted into the patient's mouth alongside their inner cheek, once the vacuum pump is initiated, the saliva and debris from the patient's mouth is sucked in from the peripheral edge 16 of the device 2 through the arced channels 42, into the trough 18, through the connection tube 26 and into the remainder of the saliva ejection system. Since the larger of the two plates, the first (inner) cheek plate 6 lies against the patent's check, there is a step down in the periphery edges of the plates and the vacuum created will not draw the patient's cheeks into contact with the peripheral edge of the saliva ejector and across the channels so as to block the flow of saliva.

Those skilled in the art will appreciate that the conception, upon which this disclosure is based, may readily be utilized as a basis for the designing of other structures, methods and systems for carrying out the several purposes of the present invention. Although described in its preferred embodiment it is known that the saliva ejection system need not have a saliva ejection device coupled to it to function as the "U" connector may draw saliva from the patient's mouth directly through its inner cheek nipple. It is important, therefore, that the claims be regarded as including such equivalent constructions insofar as they do not depart from the spirit and scope of the present invention.

I claim:

1. A saliva ejection system comprising:
    a saliva ejector for placement within a patient's mouth;
    a "U" configured hollow connector having an inner cheek nipple and an outer cheek nipple, said inner cheek nipple connected to said saliva ejector;
    a sterile tube having a distal end and a proximal end, said distal end connected to said outer cheek nipple;
    a quick connect fitting having an entrance nipple and an exit nipple; said proximal end of said sterile tube connected to said entrance nipple of said quick connect fitting;
    a non-sterile tube having a first end and a second end, said first end connected to said exit nipple of said quick connect fitting; and
    a vacuum fitting having a minor nipple and a major nipple, said second end of said non-sterile tube connected to said minor nipple wherein said saliva ejector comprises: a first and second generally planar plates having distal ends, proximal ends, an inner face, an outer face, and identically shaped perimeter edges; a suction connection tube disposed centrally between said plates and residing adjacent to said proximal ends, said connection tube having a vacuum connection end and a saliva inlet end; a series of embossings formed thereon said inner faces so as to form a series of saliva flow channels between said plates when said planar plates are conjoined and positioned in a spaced, parallel, mirror imaged configuration.

2. The saliva ejector of claim 1 wherein said planar plates are hingedly connected.

3. The saliva ejector of claim 1 further comprising a hinge operatively connected between said proximal ends of said plates.

4. The saliva ejector of claim 1 wherein said plates are ovate shaped.

5. The saliva ejector of claim 1 further comprising:
a first raised pad extending from the distal end of said first plate said first pad having an engageable trough formed thereon; and
a second raised pad extending from the distal end of said second plate, said second pad having an engageable tab formed thereon, said engageable tab configured for engagement with said engageable trough.

6. The saliva ejector of claim 5 wherein said engageable tab and said engageable trough have a dovetail configuration.

7. The saliva ejector of claim 5 further comprising an open trough formed thereon said inner faces, said trough sized for frictional engagement with said saliva inlet end of said suction connection tube in said assembled saliva ejector.

8. The saliva ejector of claim 7 wherein said embossings include a series of curved ribs, said ribs extending a first height above said inner faces of said plates.

9. The saliva ejector of claim 8 wherein said curved ribs extend between said open trough and said perimeter edges.

10. The saliva ejector of claim 9 wherein a series of saliva flow channels are formed between adjacent ribs in said assembled saliva ejector, said channels residing between said open trough and said perimeter edges.

11. The saliva ejector of claim 1 wherein assembled, said plates are held in a spaced parallel configuration with said embossings there between.

12. A saliva ejection system comprising:
a "U" configured hollow connector having an inner cheek nipple and an outer cheek nipple, said inner cheek nipple connected to said saliva ejector;
a sterile tube having a distal end and a proximal end, said distal end connected to said outer cheek nipple;
a quick connect fitting having an entrance nipple and an exit nipple; said proximal end of said sterile tube connected to said entrance nipple of said quick connect fitting;
a non-sterile tube having a first end and a second end, said first end connected to said exit nipple of said quick connect fitting; and
a vacuum fitting having a minor nipple and a major nipple, said second end of said non-sterile tube connected to said minor nipple wherein said saliva ejector comprises: a first and second generally planar plates having distal ends, proximal ends, an inner face, an outer face, and identically shaped perimeter edges; a suction connection tube disposed centrally between said plates and residing adjacent to said proximal ends, said connection tube having a vacuum connection end and a saliva inlet end; a series of embossings formed thereon said inner faces so as to form a series of saliva flow channels between said plates when said planar plates are conjoined and positioned in a spaced, parallel, mirror imaged configuration.

13. The saliva ejection system of claim 12 wherein said quick connect fitting has a central flange disposed between said entrance nipple and said exit nipple said central flange, an entrance nipple side of said central flange having a series of radially spaced stop ribs preventing said sterile tube from abutting said central flange.

14. The saliva ejection system of claim 13 wherein an exit nipple side of said central flange has series of stretcher ribs extending therefrom.

15. The saliva ejection system of claim 14 further comprising a saliva ejector, said saliva ejector comprising a first leaf shaped inner plate and a second leaf shaped cheek plate, each having distal ends, proximal ends, an inner face and an outer face, and identically shaped perimeter edges;
a suction connection tube with a pair of gusset plates extending normally from opposite sides of said connection tube, said connection tube having a vacuum connection end and a saliva inlet end, wherein said proximal ends of said first leaf shaped plate is hingedly affixed to a first side of said gusset plates and said second leaf shaped plate is hingedly affixed to a second side of said gusset plates;
a pattern of raised ribs formed thereon said inner faces, wherein said pattern of ribs on said first leaf and said pattern of embossings on said second leaf are not identical patterns;
a groove formed along a linear centerline of said plates, said groove dimensioned to accept said said saliva inlet end of said connection tube;
a first pad formed on said first plate having a having an engageable trough formed thereon configured for mating engagement with an engageable tab formed on said second plate;
wherein said saliva ejector may be assembled by folding said first plate and said second plate about said gusset plates to place said plates into a parallel, spaced configuration wherein a series of open channels are formed between adjacent ribs, said channels equally spaced about said perimeter edge.

16. The saliva ejector of claim 15 wherein said first leaf shaped plate is smaller than said second leaf shaped plate.

* * * * *